(12) United States Patent
Lemmens et al.

(10) Patent No.: US 6,638,535 B2
(45) Date of Patent: Oct. 28, 2003

(54) MODIFIED RELEASE FORMULATIONS CONTAINING A HYPNOTIC AGENT

(75) Inventors: Jacobus M. Lemmens, Mook (NL); Dennie J. M. van den Heuvel, Boxmeer (NL); Johannes J. Platteeuw, s'Hertogenbosch (NL); Frans van Dalen, Nijmegen (NL)

(73) Assignee: Synthon BV, Nijmegen (NL)

( * ) Notice: Subject to any disclaimer, the term of this patent is extended or adjusted under 35 U.S.C. 154(b) by 10 days.

(21) Appl. No.: 09/833,662

(22) Filed: Apr. 13, 2001

(65) Prior Publication Data

US 2003/0054041 A1 Mar. 20, 2003

Related U.S. Application Data

(60) Provisional application No. 60/196,939, filed on Apr. 13, 2000.

(51) Int. Cl.[7] .............................. A61K 9/20; A61K 9/14; A61K 9/16; A61K 31/44; A61K 47/00
(52) U.S. Cl. .................. 424/489; 424/490; 424/464; 424/465; 514/300; 514/781
(58) Field of Search ................. 424/489, 490, 424/464, 465; 514/300, 781

(56) References Cited

U.S. PATENT DOCUMENTS

| | | |
|---|---|---|
| 3,862,140 A | 1/1975 | Zinnes et al. |
| 4,382,938 A | 5/1983 | Kaplan et al. |
| 4,626,538 A | 12/1986 | Dusza et al. |
| 4,794,185 A | 12/1988 | Rossey et al. |
| 5,292,461 A | 3/1994 | Juch et al. |
| 5,891,891 A | 4/1999 | Benincasa |
| 6,242,460 B1 | 6/2001 | Ettema et al. |
| 6,248,363 B1 * | 6/2001 | Patel et al. .................. 424/497 |
| 6,281,360 B1 | 8/2001 | Ettema et al. |
| 6,309,668 B1 * | 10/2001 | Bastin et al. .............. 424/472 |

FOREIGN PATENT DOCUMENTS

| | | |
|---|---|---|
| EP | 0 050 563 | 5/1984 |
| EP | 0 251 859 | 11/1990 |
| WO | 00/33835 | 6/2000 |

OTHER PUBLICATIONS

Martine Schmitt et al., Imidazo [1,2–b] pyridazines. XXIII* Some 5–Deaza Analogues. Syntheses of Some 2–Aryl–6–(chloro, methoxy or unsubstituted)–3–(variously substituted)imidazo[1,2–a] pyridazines and Their Affinity for Central and Mitochondrial Benzodiazepine Receptors; Aust. J. Chem., 50:719–725 (1997).

Giuseppe Trapani et al., Synthesis and binding affinity of 2–Phenylimidazo[1,2–a] pyridazines Derivatives for both Central and Peripheral Benzodiazepine Receptors. A New Series of High–Affinity and selective ligands for the Peripheral Type; J. Med. Chem., 40:3109–3118, (1997).

P. George et al., "Zolpidem and Related Compiounds: Syntheses, Physical Properties and Structure Activity Relationships"; Imidazopyridines in sleep disorders; Raven Press, pp 11–23, (1998).

* cited by examiner

Primary Examiner—Thurman K. Page
Assistant Examiner—Amy E Pulliam
(74) Attorney, Agent, or Firm—Fleshner & Kim, LLP (57) ABSTRACT

Hypnotic pharmaceutical compositions are made from pellets and exhibit a modified release. Zolpidem or a pharmaceutically acceptable salt thereof is a typical hypnotic. The pellets are preferably spherical and exhibit a dissolution profile that includes 60% of the hypnotic agent being release from the pellet not earlier than 5 minutes from the start of a specified in vitro dissolution test. Although the modified release profile can include 50% of the hypnotic agent being released not earlier than 15 minutes after the start of the dissolution test, the pellet preferably does not contain a release rate controlling excipient or coating. Instead, microcrystalline cellulose and the active constitute the majority of the pellet, e.g. 90% or more. Spherical pellets are also made by a convenient method that is applicable to any pharmaceutically active agent.

38 Claims, 6 Drawing Sheets

MODIFIED RELEASE FORMULATIONS CONTAINING A HYPNOTIC AGENT

CROSS REFERENCE TO RELATED APPLICATIONS

This application claims the benefit of priority under 35 U.S.C. 119(e) from provisional application Serial No. 60/196,939, filed Apr. 13, 2000, the entire contents of which are incorporated herein by reference.

BACKGROUND OF THE INVENTION

1. Field of the Invention

The present invention relates to rapid acting hypnotic agents formulations, especially zolpidem, having a modified release and to various pharmaceutical forms and uses thereof.

2. Description of the Related Arts

Various rapid acting hypnotics are known for inducing or maintaining sleep. Zolpidem, an imidazopyridine having IUPAC chemical nomenclature N,N,6-trimethyl-2-(4-methylphenyl)-imidazo[1,2-s]pyridine-3-acetamide and represented by the following formula is one such hypnotic agent. The zolpidem free base was disclosed generically in EP 50563 of Synthelabo. Zolpidem tartrate was subsequently disclosed in EP 251859 (U.S. Pat. No. 4,794,185). More recently, zolpidem has been suggested as useful in treating Parkinson's disease, parkinsonian symptoms, obsessive-compulsive disorder and certain forms of dementia in U.S. Pat. No. 5,891,891, the entire contents of which are incorporated herein by reference.

Zolpidem has been marketed as an immediate release tablet for oral application under the trade marks AMBIEN® and STILNOX®. In these commercial pharmaceutical dosage forms, zolpidem is present as a salt with L(+)tartaric acid wherein the molar ratio of zolpidem to tartaric acid is 2:1. This salt is conventionally called zolpidem hemitartrate but a more correct denomination thereof, which will be used hereinafter, is zolpidem tartrate. Commercially available zolpidem tablets are conventional film coated tablets for immediate release of the active substance after ingestion and they contain 5 or 10 mg of zolpidem tartrate. The inactive ingredients are: lactose, microcrystalline cellulose, sodium starch glycolate, hydroxypropylmethylcellulose and magnesium stearate. The film coating layer consists of hydroxypropylmethylcellulose, polyethylene glycol and colorants.

Figure 1:
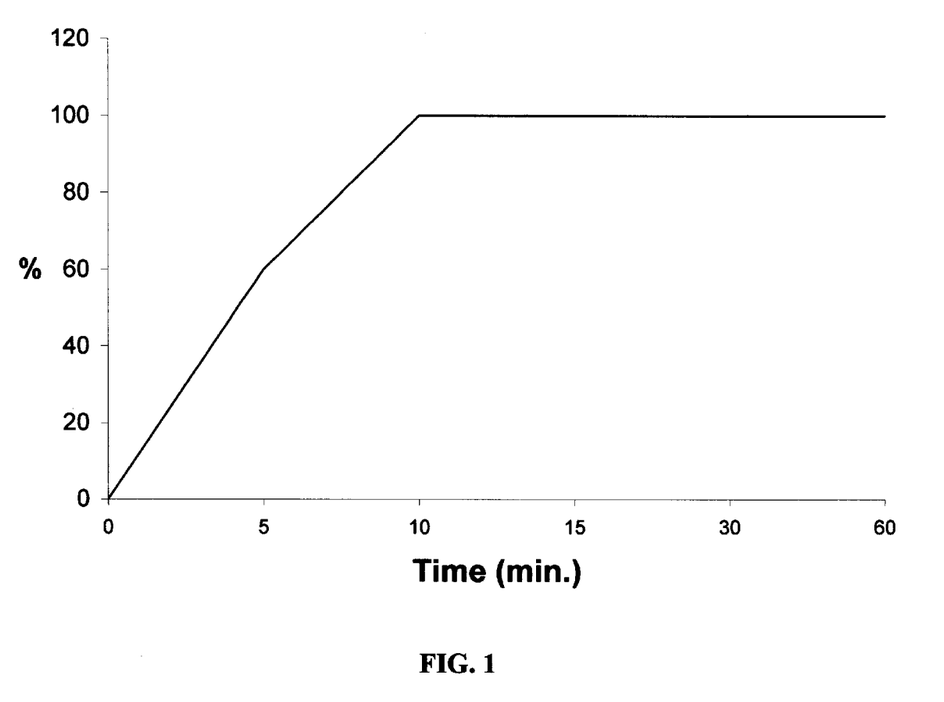
FIG. 1 shows a representative release profile of commercial zolpidem tartrate tablets

A dissolution profile (i.e., the time dependence of the zolpidem concentration in aqueous phase after the final form is placed into a standardized aqueous environment) of the commercially available tablets is shown in FIG. 1. It is apparent that the dissolution curve is characterized by quick and rapid release of the entire amount of zolpidem from the tablet. This is consistent with the presence of a disintegrating agent in the tablet, namely sodium starch glycolate. Thus, the tablet is constituted in such a way that zolpidem release is not controlled by diffusion from the tablet matrix but by dispersion; the tablet disintegrates quite rapidly in the stomach and liberates almost immediately the whole bolus of zolpidem. Consequently, the ingestion of the tablet provides initially a considerably high serum concentration of zolpidem which is then metabolized. While zolpidem is a rapidly acting hypnotic, it is also a rapidly eliminated hypnotic agent. As a result, in therapy zolpidem starts acting within 15–30 minutes after ingestion of the tablet or even earlier and its action lasts for approximately 4–6 hours.

In certain situations this onset and duration of zolpidem action is undesirable. For example, quick dissolution of whole bolus of zolpidem from the commercial tablet may cause problems in zolpidem-sensitive patients; i.e., patients whose effective sleep-inducing plasma concentration of zolpidem is either lower than the average or is reached more quickly than the average patient. As a consequence, the onset of therapeutic action of zolpidem tablets may be too quick for zolpidem sensitive persons and this could be inconvenient, e.g., such patients may not have had enough time to prepare for and lie down before falling asleep.

Zolpidem is most effective when present in plasma within a certain concentration range. Above this range, there may be a danger that deleterious side effects may become manifest and even when there is not the danger, excess drug in the blood plasma may simply be wasted. Thus, an initial blood plasma concentration that exceeds the minimum effective concentration needed for inducing sleep may not manifest a proportionate therapeutic response and, on the other hand, the excess zolpidem cannot be used later as it is already metabolized or eliminated and thus wasted. As a result, the duration of action of the available zolpidem tablets is sometimes insufficiently short and thus does not accommodate a longer, uninterrupted and deep sleep.

Mutatis mutandis, this statement is valid also for similar hypnotic agents, such as zopiclon or zaleplon, used in immediate release oral dosage forms. Zopiclon is a compound of formula (2) and has been disclosed in U.S. Pat. No. 3,862,140, while zaleplon is a compound of formula (3) and has been disclosed in U.S. Pat. No. 4,626,538.

Formula (2)

Formula (3)

Both compounds are used in pharmaceutical practice in rapid release oral compositions comprising, as the active ingredient, the respective compound in the form of its free base.

It is thus desirable to develop a pharmaceutical formulation for oral application of rapid acting hypnotic agent such as zolpidem that exhibits a fast but also a prolonged action at the same time. Delayed release and sustained release compositions and dosage forms, namely those in which a specific agent or device is present to act as a means for controlling the release rate of an active substance, are well known in the prior art. However, such conventional delayed/sustained release formulations are generally contrary to the purpose of a rapid acting hypnotic. The patient taking zolpidem desires the onset of the sleeping effect to be rapid. But a conventional sustained release formulation would delay the onset of sleep. Accordingly, the use of traditional release modifying agents such as acrylate polymers, would be expected to be inconsistent with the administration of a simple, rapid acting hypnotic dosage form.

Also, pharmaceutical compositions with proper modification of release rate are desirable when use of the rapidly acting hypnotic agent is for purposes other than for treatment of sleep disorders. For example, use of zolpidem in the above mentioned U.S. Pat. No. 5,891,891 for treating parkinsonian symptoms, should preferably provide a moderated onset and prolonged duration of the action, instead of an immediate release bolus.

SUMMARY OF THE INVENTION

As a result of thorough investigation of the matter, it has been found that rapid acting hypnotic agents, e.g., zolpidem, zopiclon, zaleplon, etc., can be formulated into a convenient pharmaceutical composition, especially into pellets, that exhibit a modified release profile which can effectively address the above disadvantages of the commercially available immediate release dosage forms.

Thus, a first aspect of the invention relates to a pharmaceutical pellet comprising a substantially homogenous mixture of a rapidly acting hypnotic agent or a pharmaceutically acceptable salt thereof and a pellet forming carrier, wherein said pellet exhibits a dissolution profile under US Pharmacopoeia XXIII, Dissolution method I, in a basket apparatus at temperature 37° C., in 0.01N HCl medium and at 100 r.p.m., that includes 60% of the hypnotic agent being released from the pellet not earlier than 5 minutes from the start of the test. Preferably, the dissolution profile includes essentially 100% of the hypnotic agent being released from the pellet not earlier than 60 minutes from the start of the dissolution test. The rapid acting hypnotic agent is typically zolpidem, zopiclon, or zaleplon, preferably zolpidem free base or zolpidem hydrogen tartrate.

A second aspect of the invention relates to a pharmaceutical unit dosage form, comprising an effective amount of the above described pellets. The dosage form is preferably a capsule, but tablets, sachets, etc., are also included.

A third aspect of the invention relates to a method of using the pellets, which comprises inducing or maintaining sleep by administering an effective hypnotic amount of the above-described pellets to a mammal, preferably a human.

A fourth aspect of the present invention relates to a new and convenient method of making pharmaceutically acceptable spherical pellets. The pellets can be made with any active ingredient, including rapidly acting hypnotic agents and is thus also suitable for making the pellets of the above-described first aspect of the invention, but is not limited thereto. A process for making pharmaceutically acceptable spherical pellets, which comprises (1) combining a solvent, a pharmaceutically active agent and/or its pharmaceutically acceptable salt, and at least one pellet forming carrier to form a wet mixture, wherein the solvent is not combined by spraying; (2) stirring, chopping, or both, the wet mixture to form monolithic, spherical wet pellets; and (3) drying the wet pellets to form the intended pharmaceutically acceptable pellets.

Preferred embodiments of the present invention provide a composition that moderates the rapid release occurring in the commercial tablets to such extent that the possible initial over concentration of active agent in the body fluids is minimized and that the hypnotic action is reasonably delayed to overcome a shortage of sleep. Surprisingly it has been discovered that an oral composition based on a pellet is suitable for obtaining the desired modified release of the hypnotic agent.

DETAILED DESCRIPTION OF THE INVENTION

The present invention relates to modified release pharmaceutical compositions containing a rapidly acting hypnotic agent. The composition is in the form of a pellet or a final dosage form (unit dosage form) derived therefrom. The term "pellet" as used herein means solid spherical or non-spherical particles having an average particle size (diameter) of about 0.1 to 2.5 mm, more typically 0.1 to 2.0 mm. Non-spherical particles are sometimes referred to in the literature as "granulates" or "granules." For simplicity, both the spherical and non-spherical forms are generically referred to herein as "pellets" unless specifically indicated to the contrary.

The pharmaceutical pellets of the present invention exhibit a dissolution profile under US Pharmacopoeia XXIII, Dissolution method I, in a basket apparatus at temperature 37° C., in 0.01N HCl medium and at 100 r.p.m., that includes 60% or less of the hypnotic agent being released from the pellet not earlier than 5 minutes from the start of the test. This means that the pellets do, in fact, release the hypnotic agent thereby exhibiting a release profile and further the profile is one that satisfies the relationship that 60% or less of the agent is released not sooner than five minutes after the start of the identified in vitro dissolution test. This release profile distinguishes the pellets of the present invention from immediate release tablets. Normally, essentially 100% of the hypnotic agent is released from the pellets not earlier than 60 minutes after the start of the dissolution test. The "essentially 100%" release means that all or nearly all of the hypnotic agent that is going to be released from the pellet has been released; it being understood that in some embodiments it is possible for a small amount of the hypnotic agent to not be released from the pellet, and in any event is usually in the range of 95 to 100% of the total amount of the hypnotic agent present in the pellets.

The release profile for pellets of the present invention typically, but not necessarily, includes 80%, preferably 60%, more preferably 40% of the hypnotic agent being released from the pellets not sooner than 10 minutes after the start of the dissolution test. Similarly, preferred forms of the pellets of the invention exhibit a release profile that includes 85%, preferably 70%, more preferably 50%, still more preferably 40% of the hypnotic agent being released from the pellet of the invention not sooner than 15 minutes from the start of the dissolution test.

On the other hand, while the dissolution profile normally includes essentially 100% of the hypnotic agent being released from the pellets not earlier than 60 minutes after the start of the dissolution test, preferably essentially 100% is released within 1 to 5 hours, more preferably 2 to 4 hours after the start of the dissolution test. In some embodiments, the essentially 100% release is achieved at around 3 hours or 2.5 to 3.5 hours.

It should be noted that these dissolution profile characteristics refer to the pellet(s) and not necessarily to the final dosage form such as a capsule, which typically provides an initial delay of several minutes before the pellets are exposed to the release medium. For convenience, a plurality of pellets can be tested at the same time, the results describing the average pellet. The plurality can be an entire population obtained from a batch or a segment thereof such as a sample or a select grouping; e.g., a certain size range of pellets.

Preferably the hypnotic agent is released predominantly by diffusion; i.e., diffusion release after the initial pellet surface (exterior) amount of hypnotic agent, if any, is dissolved. Preferably the pellets of the present invention exhibit such diffusion release by twenty minutes after the start of the dissolution test, more preferably by 10 minutes after the start of the dissolution test.

The pharmaceutical pellets of the present invention comprise a substantially homogeneous mixture of a rapidly acting hypnotic agent or a pharmaceutically acceptable salt thereof and a pellet forming carrier. The "homogeneous mixture" can be throughout the entire pellet or in a significant layer of the pellet. For example, the pellet can be built up on a seed, typically a sugar seed, by forming one or more coatings of the homogenous mixture of hypnotic agent and pellet forming carrier to form a homogenous mixture layer surrounding the seed. Preferably, however, the pellet is "monolithic" meaning that the homogeneous mixture extends throughout the pellet, including the central core; i.e., no inert seed is present within the pellet. The monolithic pellet may nonetheless have a surface coating as is discussed more fully hereinafter.

Rapidly acting hypnotic agents are well known in the art and are generally characterized by being capable of providing a quick onset of hypnotic effect, e.g. less than approximately 30 minutes. Examples of rapidly acting hypnotic agents include zolpidem, zopiclon, zaleplon, and benzodiazepines. The agents can be used in the free base form or as a pharmaceutically acceptable salt thereof. Examples of suitable salts include hydrochloride, hydrobromide, maleate, fumarate, tartrate, hydrogentartrate, sulfate and sulfonates such as mesylate or tosylate. The salts may be crystalline or amorphous and they may be either water soluble or water insoluble. In this regard the zolpidem salts disclosed in co-pending U.S. application Ser. No. 09/449,974, filed Nov. 26, 1999, the entire contents of which are incorporated herein by reference, are contemplated as being useful in compositions of the present invention. Specific examples of zolpidem salts include zolpidem hydrochloride, zolpidem hydrochloride monohydrate, zolpidem hydrochloride ethanolate, zolpidem methane sulfonate, zolpidem tosylate, zolpidem maleate, zolpidem hydrobromide, zolpidem fumarate, zolpidem sulfate, zolpidem tartrate and zolpidem hydrogen tartrate. Preferably the agent is selected from zolpidem free base, zopiclon free base, zaleplon free base, zolpidem hydrogen tartrate (meaning a zolpidem to tartrate ratio of substantially 1:1), and zolpidem hydrochloride.

Pellet forming carriers can be any matrix forming material that facilitates pellet formation. While the carrier material can be water soluble, generally the material is water insoluble or slightly water soluble. Preferably the pellet carrier material is water insoluble and furthermore is also insoluble in gastrointestinal solutions, both real and simulated. Typically, the carrier material forms a non-disintegrating, non-dissolving, porous matrix. After oral administration, the active substance is liberated from the pellet-forming carrier into the body fluids while the carrier remains basically intact. Examples of pellet forming carriers include microcrystalline cellulose, hydroxypropyl methylcellulose (HPMC), hydroxypropyl cellulose (HPC), PLGA, dextrines, etc. The preferred pellet forming carrier is microcrystalline cellulose.

In addition to the hypnotic agent and pellet forming carrier, the homogeneous mixture and/or the pellet can contain additional pharmaceutically acceptable excipients such as carriers, binders, lubricants, fillers, etc. In more detail, the pellets can contain one or more wetting agents such as sodium lauryl sulfate, cetyl alcohol, docusate sodium, polyoxylene alkyl ethers etc., lubricants such as magnesium stearate, colloidal silicon dioxide, sodium stearyl fumarate, etc., inert fillers such as ethyl cellulose, maltodextrin, dextrans, chitosans, etc. and plasticizing agents such as triethyl citrates, dibutyl phthalate, glycerol, triacetin, castor oil, polyethylene glycol, etc. Disintegration agents are not required in the composition of the present invention and are preferably excluded from the pellets as such agents would usually interfere with the desired modified release dissolution profile.

It is a particular aspect of the invention to provide a pharmaceutical pellet containing a hypnotic agent such as zolpidem characterized in that it does not contain a release rate controlling excipient or coating which would delay the release of the main portion of zolpidem to the time when the dosage form passes to lower parts of the gastrointestinal tract. It is however not excluded that the pellets of the invention contain minor amounts of certain known rate-controlling agents. For example, the carrier may be combined with release controlling agents, as are well known in the prior art such as acrylate polymers, PVA, PVP, povidone, crosspovidone, etc. However, the presence of these rate controlling agents is basically not necessary and is preferably excluded from the pellets of the invention; i.e. neither the pellet forming carrier nor the optional pellet coating contains a rate controlling polymeric material or other rate controlling excipient or device.

The pellets of the invention may be coated by a thin film coating to prevent undesired action of the external environment during handling and storage and to enhance physical properties of the pellet. It must however be pointed out that this film coating should be rapidly dissolvable in the stomach environment (a non-enteric coating) to minimize the latent period prior to release and should not have any other influence on the release characteristics. Typically any coating on the pellets serves only for "cosmetic" purposes such as taste masking, surface improvement, etc. Nonetheless, the pellets usually do not contain any kind of surface coating.

The amount of rapidly acting hypnotic agent and/or its pharmaceutically acceptable salt in the pellet composition is not particularly limited and can be varied in such extent that the final pellets still possess proper physical parameters, such as hardness or friability, required for formulating into a final dosage form. The pellet is usually comprised of from 1 to 50%, more typically from 5 to 50%, typically 5 to 20% such as about 10%, by weight, of the hypnotic agent, especially of zolpidem or its pharmaceutically acceptable salt, measured as the free base. Preferably the pellets are composed mainly of the hypnotic agent and the pellet forming carrier. For example, the total amount of hypnotic agent and carrier is preferably at least 90% of the pellet weight, preferably at 95% of the pellet weight. A typical two component pellet composition consists of:

microcrystalline cellulose (50–95%); and zolpidem in a form of free base, hydrochloride, tartrate, hydrogentatrate or methane sulfonate (5–50%);

without any other inactive ingredient.

The modified release of hypnotic agent exhibited by pellets of the present invention can be obtained by choosing proper excipient(s) including the pellet forming carrier, and/or by the solubility of the hypnotic agent in body fluids, as well as by choosing the size or diameter of the pellets and other process parameters in forming the pellets. For example, by varying the proportion of the composition's excipients relative to each other and to the amount, nature and/or particle size of the zolpidem active substance, pellets with different dissolution profiles may be obtained. The water solubility of the hypnotic agent or its salts as well as pellet size (diameter) and surface area of pellets are also factors that affect and/or control the release rate. In this respect, use of water insoluble salts or the free base of zolpidem in the form of pellets has certain advantages in slowing the dissolution profile relative to an immediate release tablet of zolpidem tartrate. Similarly, larger pellets generally have a longer release time than smaller pellets. By providing more total surface area, smaller pellets generally have more hypnotic agent available to be readily dissolved into the medium. Further, active agent within a smaller pellet will generally have a shorter pathway to the dissolution medium than active agent within a larger pellet. The release rate of hypnotic agent is thus generally faster with smaller pellets than with larger pellets. It is believed that the density/porosity of the pellet can also affect the dissolution profile with more dense/less porous pellets providing for longer release times.

The pellets of the invention can be prepared by standard pellet forming methods known in the art. In general, the pellets are formed by a wet granulation technique. These techniques are based on granulation (pelletization) of a moistened mixture of the hypnotic agent, the pellet forming carrier(s), and, optionally, any other excipient(s) in a mixer-granulator followed by drying. Water or other suitable solvent is needed in the manufacturing process but it is removed, essentially completely, after formation of pellets. Particularly suitable are processes in which the unit operations of mixing, pellet forming, and drying can be performed in one piece of equipment, typically in a high-shear mixer-granulator. Suitable high-shear mixer granulators include the "VAGUMATOR" by Bohle, i.e. the VMA-10, VMA-20, etc. Under proper conditions of temperature, mixing, stirring and drying, spherical pellets or irregular granules are formed.

A preferred process for making spherical pellets comprises (1) combining a solvent, a pharmaceutically active agent and/or its pharmaceutically acceptable salt, and at least one pellet forming carrier to form a wet mixture, wherein the solvent is not combined by spraying; (2) stirring, chopping, or both, the wet mixture to form monolithic, spherical wet pellets; and (3) drying the wet pellets to form the intended pharmaceutically acceptable pellets. The process can be used to make pellets containing rapidly acting hypnotic agents as described above, but is not limited thereto. Any pharmaceutically acceptable active agent can be formulated into a pellet having the desired modified release profile, such as those described above for rapid acting hypnotic agents, by the preferred process of the present invention.

The first step makes a wet mixture containing the active agent, pellet forming material, and solvent. These ingredients can be combined in any order to make the wet mixture. For example, the solvent can be dumped onto a dry blend, preferably a homogenous blend, of the active and pellet forming carrier. Alternatively, the active and pellet forming carrier can be added, either separately or together, to the solvent. While the active and pellet forming carrier are normally combined with the solvent as dry powders, more typically as a pre-blend of dry powder, such is not required in that the active could be combined with the solvent to form a solution or suspension which is in turn combined with the pellet forming carrier. Thus, the combining step can be carried out as one step or as a series of steps. The expression "wherein the solvent is not combined by spraying" means that the solvent is not forced to be contacted with the active or pellet forming carrier as slow streams, droplets or mist, such as by sending the solvent through a spray nozzle. Preferably the solvent is combined without the use of a flow restraining device of any kind (unrestricted flow) and instead pump speed provides the limit on how fast the solvent is added. This lack of spraying or a spray nozzle can allow the solvent to carry the active or other excipient without the risk of clogging the spraying appliance.

In embodiments where the solvent is dumped onto a powder of active and/or pellet forming carrier, the solvent is typically added at a rate of one liter per 1 to 1200 seconds, more typically one liter per 20 to 120 seconds. The solvent can be added all at once or in discrete stages, e.g., discrete dumps several minutes apart and even after stirring/chopping is underway. Where the solvent is already charged to the vessel before the active or pellet forming carrier is added, additional solvent can be dumped in if needed.

The solvent is typically water, but any liquid can be used including organic solvents such as ethanol, and supercritical fluids such as carbon dioxide at low temperature and under high pressure. The active agent is not particularly limited and includes acarbose, alprostadil, amlodipine, artemotil, atorvastatine, benzodiazepines, citalopram, cladribine, clopidrogel, candesartan, carvedilol, desogestrel, dexrazoxane, diltiazem, dofetilide, donepezil, eprosartan, etanercept, etidronate, exemestane, latanoprost, leflunomide, letrozole, lovastatin, mirtazepine, modafinil, nateglinide, nimesulide, nizatidine, olanzapine, olopatidine, orlistat, oxybutynin, pramipexol, paroxetine, pioglitazone, quetiapine, reboxetine, remoxepride, repaglinide, risperidon, rizatriptan, ropinirol, rosiglitazone, simvastatin, tamsulosin, telmisartan, tibolon, thalidomide, tolterodine, venlafaxine, zaleplon, ziprasidone, zolpidem, zonisamide, zopiclon, and pharmaceutically acceptable salts thereof. The pellet forming carriers are as described above. The wet mixture may additionally contain other pharmaceutically acceptable excipients.

The wet mixture is then granulated into a pellet by stirring, chopping or both. This operation is preferably carried out with high speed stirring and/or chopping and should continue to be carried out even if the material appears to be agglomerating into a size that is too large. It has been unexpectedly found that continued stirring/chopping, optionally with the addition of more water, usually results in the successful formation of high quality spherical pellets, despite the initial or intermediate appearance of unacceptable agglomeration/large particle size. The stirring and/or chopping are carried out as long as needed and typically within the range of 1 to 60 minutes, more commonly from 5 to 20 minutes, depending on inter alia the size of the apparatus, the speed of the impeller, etc.

Drying can be performed by any known process and specifically includes heating such as heating the vessel that contains the wet pellets, applying microwave or infrared energy, applying vacuum or reduced pressure, passing an inert, optionally heated, gas over the wet pellets, or a combination thereof. Preferably the pellets are dried by heating under reduced pressure while passing nitrogen gas over the pellets and applying microwave energy. Infrared energy can be substituted or added to the microwave energy.

All of the process steps are preferably performed in a high shear mixer granulator apparatus. The process steps can be carried out as discrete steps in sequential order or as overlapping/concurrent steps. For example, the mixing of the active and pellet forming carrier to form a dry blend can be continued while the water is added thereby converting the blending step into the stirring or chopping step that results in pellet formation. Further, as mentioned above, additional solvent can be added even after the granulating phase of the process is underway, including interrupting the stirring or chopping (stopping the impellor) to add solvent. Each step can be carried out as one step or as a series of multiple steps. For example, the drying step can be carried out in several phases with different techniques or combinations thereof applied in the different phases.

The parameters used in making the pellets of the present invention, especially in the above-described preferred process, can affect and/or achieve the desired dissolution profile; i.e. without the use of a release rate controlling excipient or coating. For instance, the rate at which the solvent is dumped as well as the rate of drying (solvent removal) can affect the particle size and release profile. In general, faster solvent addition favors the formation of larger pellets which in turn slows the dissolution profile. Moreover, faster solvent addition is believed to provide pellets of any given size with slower dissolution profiles in comparison to pellets of the same size but made with slower solvent addition rates. This effect is believed to be caused by increasing the density of the pellets. The drying time as well as the final solvent content can also affect the dissolution profile. Preferably drying is carried out as rapidly as possible with the final pellets containing 5% solvent or less, more preferably 3% or less. Interestingly, the size of the apparatus, that is the mixing vessel where the stirring/chopping is carried out, can affect the dissolution profile, with smaller vessels producing slower release rates. While not fully understood, it is believed that the smaller vessels allow for more energy to be applied to the pellet during formation and thus may provide for greater density or lower porosity. Other factors that affect the dissolution profile include the solubility of the active selected as well as the nature of the pellet forming carrier. For example, the initial particle size of the microcrystalline cellulose may affect the dissolution profile of the finished pellet.

The pellets of the present invention can be formulated for per oral application in suitable unit dosage forms by methods known in the art. A "unit dosage form" means a form in which a single dose of a plurality of pellets bearing the hypnotic agent is orally administered to a patient and which contains the desired therapeutic amount of agent. Suitable unit dosage forms include capsules, tablets, sachets, etc. The preferred unit dosage form is a capsule, particularly a hard gelatin capsule, into which the pellets of the invention are filled in appropriate amounts. The capsules could also be made of gelatin/polyethylene glycol, starch, hydroxypropyl methylcellulose or other suitable capsule-forming materials.

The pellets may also be compressed into tablets using a binder and/or hardening agent commonly employed in tabletting (such as microcrystalline cellulose or a co-crystallized powder of highly modified dextrins and sucrose (DI-PAC™)). In one embodiment, the tablet would contain a disintegrant which would allow the swallowed tablet to quickly disintegrate thereby releasing the plurality of pellets. The surface of such a tablet should not be coated or, if coated, should be coated only by a rapidly soluble thin film coating. Enteric coating or other coating that would interfere with release in the stomach should be avoided.

The unit dosage form of the present invention contains a pharmaceutically effective amount of the pellets of the invention. Generally, the unit dosage form contains 1 to 50 mg, preferably 2.5 to 50 mg, typically 2.5 to 20 mg, of the hypnotic agent, expressed in terms of the free base of the hypnotic agent. An examplary unit dosage form comprises about 4 or about 8 mg of zolpidem or its pharmaceutically acceptable salt.

As pointed out above, pellets of different size can exhibit different release rates. In some embodiments, it is desirable to select a specific size range or ranges of pellets for making the unit dosage form. The pellets can be separated by sieving or other suitable means into appropriate size ranges. For example, pellets which are generally within the range of 0.1 to 2.0 mm or larger, can be separated into the following size ranges: >1.7 mm; 1.4–1.7 mm; 1.18–1.4 mm; 1.0–1.18 mm; 0.85–1.0 mm; 0.71–0.85; 0.5–0.71; and <0.5 mm. One or more of these size ranges can be used in making the unit dosage form depending on the modified release characteristics desired. Further, pellets from different populations made under different conditions or with different amounts of hypnotic agent can be used in combination. The ratio of the two or more populations or segments thereof as well as the amount of hypnotic agent in each population or segment thereof can be varied as desired to control the dissolution profile of the unit dosage form. Preferably, the unit dosage form uses pellets from one type of population, e.g., one or more segments from a single production population or from multiple similar production populations made using similar or identical conditions and ingredients. While pellets can range from 0.1 to 2.5 mm, generally the preferred size (diameter) of the pellets is from 0.5 to 2.0 mm, more preferably from 0.85 to 1.7 mm, still more preferably 1.0 to 1.7. Thus, a particularly advantageous unit dosage form of the invention comprises an effective amount of monolithic pharmaceutical pellets comprising microcrystalline cellulose and a rapid acting hypnotic agent such as zolpidem, zopiclon or zaleplon, having an average diameter from 0.5 to 2.0 mm, preferably 1.4–1.7 mm.

The unit dosage forms containing the pellets of the present invention exhibit a modified release of the hypnotic agent. A preferred zolpidem-containing unit dosage form contains about 4 or 8 mg of zolpidem or a pharmaceutically acceptable salt thereof, expressed in terms of the free base, and exhibits a dissolution profile under US Pharmacopoeia XXIII, Dissolution method I, in a basket apparatus at temperature 37° C., in 0.01N HCl medium and at 100 r.p.m., such that at 15 minutes from the start of the dissolution test, 3 mg or less, or, 6 mg or less, respectively, of zolpidem is released. More preferably, the unit dosage form releases 2.5 mg or less, or, 5 mg or less, respectively, of the zolpidem at the 15 minute mark and essentially 4 mg or 8 mg, respectively, is released 5 hours or less, preferably within 3 to 4.5 hours, from the start of the dissolution test. The zolpidem is preferably in the form of zolpidem hydrogen tartrate or zolpidem free base, all amounts being expressed in terms of the free base. These release rates are readily attainable by selecting an appropriate zolpidem pellet in accordance with the present invention.

The pellets of the present invention can be used in a method for inducing or maintaining sleep and/or in methods of treatment of sleep disorders. Such method comprising administering an effective hypnotic amount of the pellets to a mammal, including human and non-human mammals. Typically, the pellets are administered orally via a unit dosage form as described above. Similarly, the unit dosage forms containing or derived from the zolpidem-containing pellets of the present invention can be used in methods for treating Parkinson's disease, parkinsonian syndromes and other disorders treatable by zolpidem by administering an effective amount of the pellets to a patient in need thereof.

The pellets may be administered in dosage amounts and regimens corresponding to those known and recommended in the art. However it is anticipated that a single dose of pellets of the present invention may contain a lower amount of the active substance in comparison with that in the commercially available immediate release dosage form due to the advantageous release rate and, consequently, due to the expected advantageous blood plasma concentration profile which could maintain the necessary concentration of zolpidem more effectively. In this way the potential side effects of a hypnotic agent could be decreased.

The invention will be further illustrated by way of the following non-limiting examples.

EXAMPLES

Example 1

Preparation of Pellets with Zolpidem Hydrochloride

| Composition: | |
|---|---|
| Microcrystalline cellulose | 1703 g |
| Zolpidem hydrochloride hydrate | 189.2 g |
| Purified water | 1892 ml |

Equipment:

High speed mixer/granulator having a 20 liter vessel (VMA-20)

Process:

microcrystalline cellulose and zolpidem hydrochloride hydrate are added into the mixer and the powder mixture is blended under inert atmosphere.

the whole amount of water is added to the mixture under stirring.

the resulting mixture is stirred for 15 minutes.

water is removed and the resulted pellets are dried as well, by employing enhanced temperature and vacuum for 4 hours.

produced pellets are fractionated by sieving.

Examples 2–4

Figure 2:
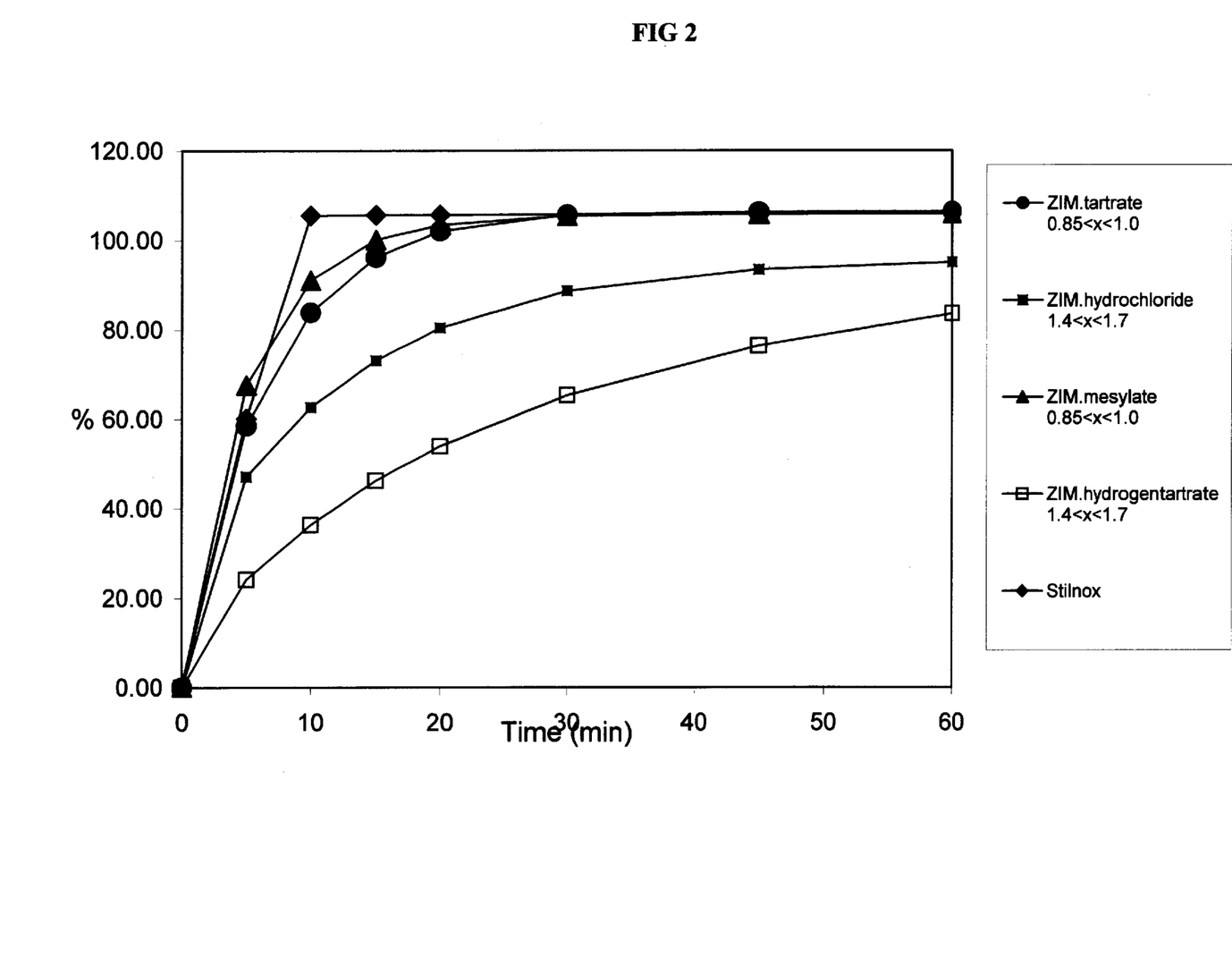
FIG. 2 shows representative release profiles for pellets prepared according to Examples 1–4 in comparison with commercial zolpidem tablets.

Using the same process as in Example 1 and employing proportional amounts of other salts of zolpidem, the following pellets are prepared:

2—Pellets with zolpidem tartrate
3—Pellets with zolpidem hydrogentartrate
4—Pellets with zolpidem mesylate Analytical Testing:

The dissolution profile of pellets in Examples 1–4 and of marketed zolpidem tablets are tested by the dissolution test in US Pharmacopoeia XXIII, Method I, in a basket apparatus at 100 r.p.m. and 37° C., in 900 ml of 0.01N HCl. The dissolved amount of zolpidem at any given time point was determined by a UV-method. Representative results are shown in FIGS. 1 and 2. When comparing with the commercial tablet of zolpidem tartrate, it is apparent that the release rate can be significantly modified by the inventive pellets of Examples 2–4. The shape of the release curve shows that, contrary to the marketed tablet, zolpidem can be gradually released for an extended period of time.

Example 5

Preparation of Pellets with Zolpidem Free Base

| Composition: | |
|---|---|
| Microcrystalline cellulose (Avicel PH-101) | 919 g |
| Zolpidem free base | 80.3 g |
| Purified water | 1006.5 ml |

Equipment:

high-speed mixer/granulator of 10 liter vessel volume (VMA-10)

Process:

microcrystalline cellulose and zolpidem are added into the mixer and the powder mixture is blended under inert atmosphere for 8 minutes.

806.5 ml of the water is added to the mixture via the spray channel with spray nozzle removed under stirring in 38 seconds.

the resulting mixture is granulated for 3 minutes, stopped, the product scraped down the walls and the remaining 200 ml of water added, the vessel closed and granulation resumed for a total of 10 minutes.

water is removed by heating, applying microwave energy, passing nitrogen over the pellets and using vacuum for 2 hours.

produced pellets contain less than 4% water and are fractionated by sieving. Fraction of between 0.85 and 1.00 mm accounts for 78% of the pellets with a total yield of 99.8%.

Gelatin capsules are filled with the pellets to make a total weight of 105+/−5 mg.

Figure 3A:
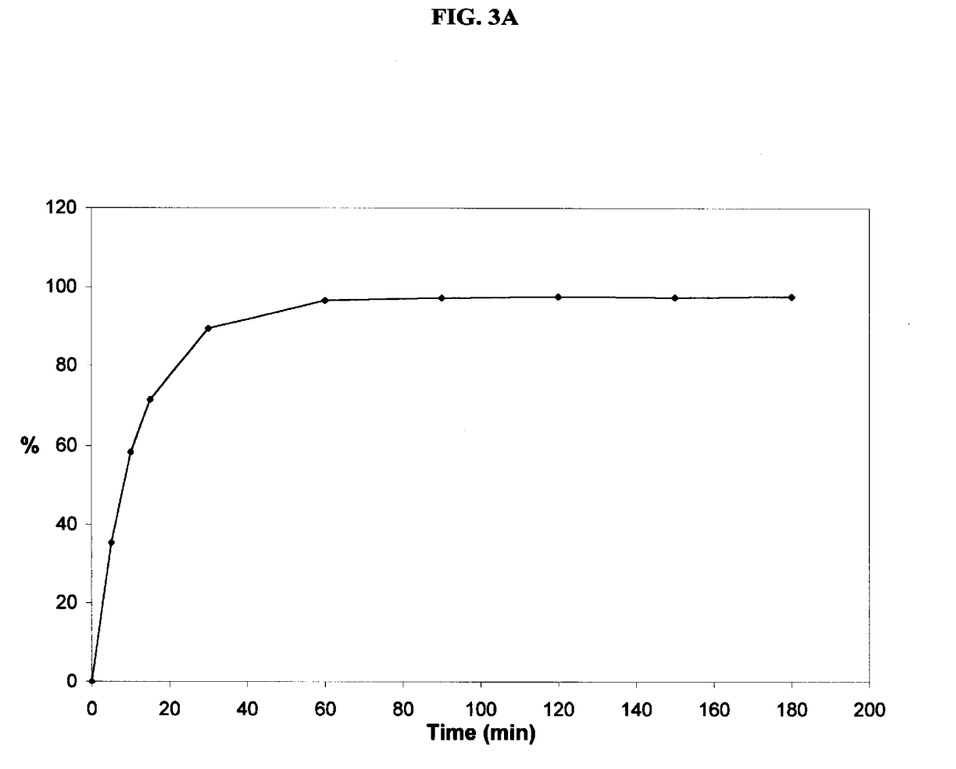
FIGS. 3A and 3B show a representative release profile for the pellets according to Example 5 having a pellet size of 1.4–1.7 mm and 0.85–1.00 mm, respectively.
Figure 3B:
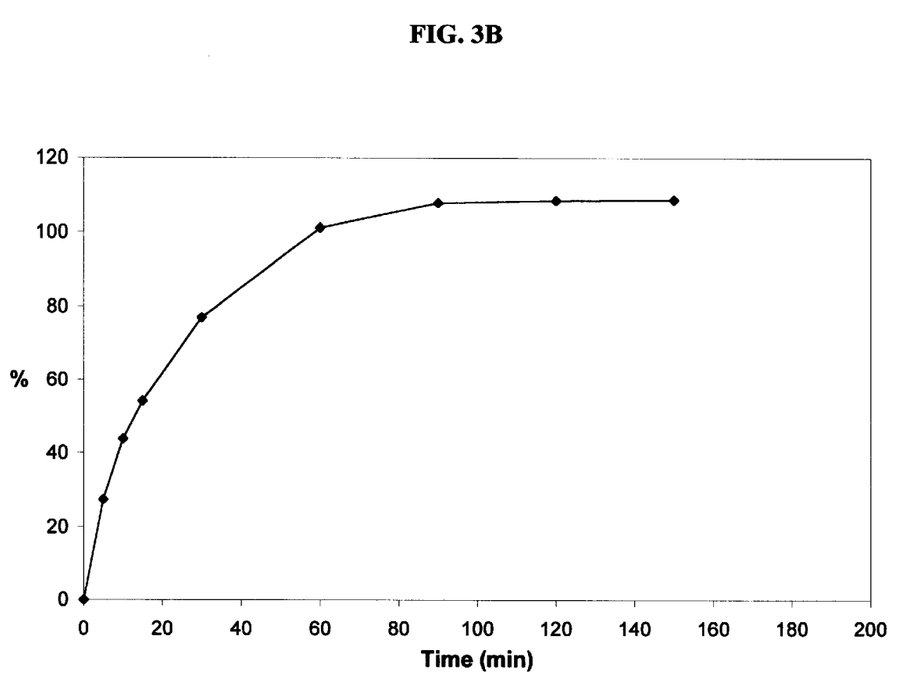

Analytical:

A representative release profile for the pellets measured as described for Example 2 is shown in FIG. 3A for the pellet fraction having a size 1.4 to 1.7 mm and in FIG. 3B for pellet fraction having a size of 0.85 to 1.00 mm.

Example 6

The process of example 5 was essentially repeated, except all of the water was added to the blended mixture within 70 seconds.

Pellet fraction of 1.18–1.40 mm accounts for 59.4% of the pellets with a total yield of 89%.

Example 7

Preparation of Pellets with Zolpidem Hydrogentartrate

| Composition: | |
|---|---|
| Microcrystalline cellulose (Avicel PH-101) | 882.7 g |
| Zolpidem hydrogentartrate | 119.8 g |
| Purified water | 1197.2 ml |

Equipment:

high-speed mixer/granulator of 10 liter vessel volume (VMA-10)

Process:

Essentially the process as used in Example 6 is followed except all of the water is added under stirring in 80 seconds and water is removed by drying for 2.5 hours.

The produced pellets are fractionated by sieving. The fraction of 1.4 to 1.7 mm is the largest and accounts for 23% of the pellets with an overall yield of 99.8%.

Gelatin capsule is filled with the pellets to make a total weight of 105+/−5 mg.

Figure 4A:
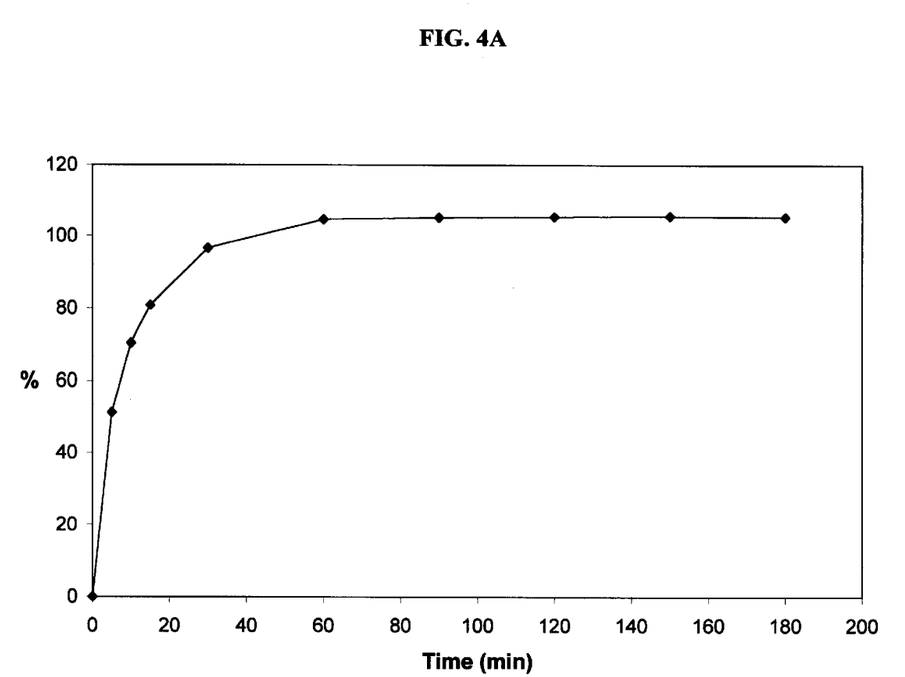
FIGS. 4A and 4B show a representative release profile for the pellets according to Example 7 having a pellet size 0.85–1.00 mm and 1.4–1.7 mm, respectively.
Figure 4B:
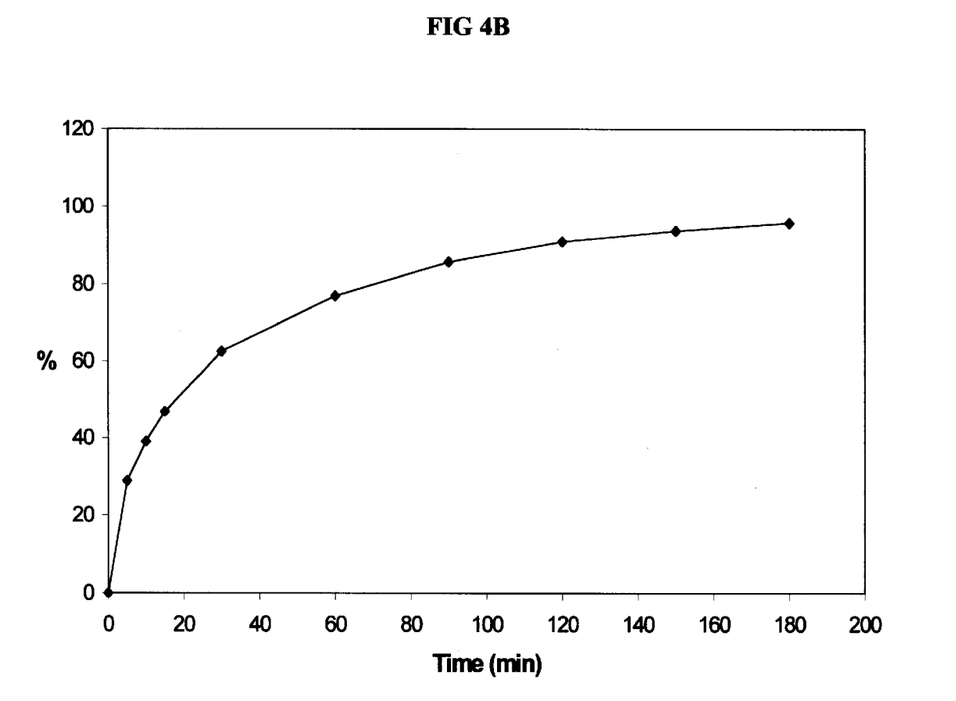

Analytical:

A representative release profile for the pellets measured as described for Example 2 is shown in FIG. 4A for the pellet fraction having a size 0.85 to 1.00 mm and in FIG. 4B for pellet fraction having a size of 1.4 to 1.7 mm.

Example 8

Preparation of Pellets with Zopiclon

| Composition: | |
|---|---|
| Microcrystalline cellulose (Avicel PH-101) | 925.0 g |
| Zopiclon | 75.2 g |
| Purified water | 1007.1 ml |

Equipment:

high-speed mixer/granulator of 10 liter vessel volume (VMA-10)

Process:

microcrystalline cellulose and zopiclon are added into the mixer and the powder mixture is blended under inert atmosphere for 8 minutes.

half amount of water is added to the mixture under stirring in 4 minutes, the rest added after the material is observed to stick to the walls, quickly.

the resulting mixture is stirred for 15 minutes total.

water is removed and the resulted pellets are dried as well, by employing enhanced temperature and vacuum for 3 hours.

produced pellets are fractionated by sieving with 1.18 to 1.4 mm being the main fraction.

Gelatin capsules are filled with the pellets to a total weight of 105+/−5 mg.

Example 9

Preparation of Pellets with Zaleplon

| Composition: | |
|---|---|
| Microcrystalline cellulose (Avicel PH-101) | 950.0 g |
| Zopiclon | 95.1 g |
| Purified water | 1000.4 ml |

Equipment:

high-speed mixer/granulator of 10 liter vessel volume (VMA-10)

Process:

microcrystalline cellulose and zaleplon are added into the mixer and the powder mixture is blended under inert atmosphere for 8 minutes.

water is added to the mixture under stirring in 60 seconds.

the resulting mixture is stirred for 10 minutes.

water is removed and the resulted pellets are dried as well, by employing enhanced temperature and vacuum.

produced pellets are fractionated by sieving with the fraction between 1.18 and 1.4 mm being the largest.

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A pharmaceutical pellet comprising a substantially homogenous mixture of a rapidly-acting hypnotic agent or a pharmaceutically acceptable salt thereof and a pellet forming carrier of microcrystalline cellulose, wherein the amount of said hypnotic agent and said pellet forming carrier is at least 90% of the pellet weight, said pellet having a particle size within the range of 0.85 to 2.0 mm and wherein said pellet exhibits a dissolution profile under U.S. Pharmacopoeia XXIII, Dissolution method I, in a basket apparatus at temperature 37° C., in 0.01N HCl medium and at 100 r.p.m., such that at 5 minutes from the start of the test, less than 60% of the hypnotic agent has been released from the pellet.

2. The pellet according to claim 1, wherein said dissolution profile further comprising essentially 100% of the hypnotic agent being released from the pellet not earlier than 60 minutes from the start of the dissolution test.

3. The pellet according to claim 1, wherein said profile further comprising 80% of the hypnotic agent being released not earlier than 10 minutes from the start of the dissolution test.

4. The pellet according to claim 1, wherein said profile further comprising 85% of the hypnotic agent being released not earlier than 15 minutes from the start of the dissolution test.

5. The pellet according to claim 4, wherein said profile further comprising 70% of the hypnotic agent being released not earlier than 15 minutes from the start of the dissolution test.

6. The pellet according to claim 5, wherein said profile further comprising 50% of the hypnotic agent being released not earlier than 15 minutes from the start of the dissolution test.

7. The pellet according to claim 6, wherein said profile further comprising 40% of the hypnotic agent being released not earlier than 15 minutes from the start of the dissolution test.

8. The pellet according to claim 4, wherein said profile further comprising essentially 100% of the hypnotic agent being released within the range of 1 to 5 hours from the start of the dissolution test.

9. The pellet according to claim 8, wherein said profile further comprising essentially 100% of the hypnotic agent being released within the range of 2 to 4 hours from the start of the dissolution test.

10. The pellet according to claim 5, wherein said profile further comprising essentially 100% of the hypnotic agent being released within the range of 1 to 5 hours from the start of the dissolution test.

11. The pellet according to claim 1, wherein said hypnotic agent is selected from the group consisting of zolpidem, zopiclon, zaleplon, and benzodiazepines.

12. The pellet according to claim 2, wherein said hypnotic agent is selected from the group consisting of zolpidem, zopiclon, and zaleplon.

13. The pellet according to claim 4, wherein said hypnotic agent or pharmaceutically acceptable salt thereof is selected from the group consisting of zolpidem, zolpidem hydrochloride, zolpidem hydrochloride monohydrate, zolpidem hydrochloride ethanolate, zolpidem methane sulfonate, zolpidem tosylate, zolpidem maleate, zolpidem hydrobromide, zolpidem fumarate, zolpidem sulfate, zolpidem tartrate and zolpidem hydrogen tartrate.

14. The pellet according to claim 1, wherein said pellet does not contain a release rate controlling excipient or coating.

15. The pellet according to claim 1, wherein said pellet is monolithic.

16. The pellet according to claim 15, wherein said pellet does not contain a surface coating.

17. The pellet according to claim 6, wherein said pellet does not contain a release rate controlling excipient or coating.

18. The pellet according to claim 17, wherein said pellet is monolithic.

19. The pellet according to claim 18, wherein said pellet does not contain a surface coating.

20. The pellet according to claim 1, wherein said pellet does not contain a disintegrant.

21. The pellet according to claim 1, wherein said pellet contains from about 1 to about 50% by weight of said hypnotic agent.

22. The pellet according to claim 2, wherein said pellet contains from about 5 to about 50% by weight of zolpidem.

23. The pellet according to claim 22, wherein said pellet-forming carrier is a microcrystalline cellulose and the total amount of zolpidem and the carrier is at least 90% of the pellet weight.

24. A pharmaceutical unit dosage form, comprising an effective amount of the pellets according to claim 1.

25. The dosage form according to claim 24, wherein said dosage form contains from about 1 to about 50 mg of said hypnotic agent, expressed in terms of the free base.

26. The dosage form according to claim 25, wherein said dosage form contains from about 2.5 to about 50 mg of said hypnotic agent, expressed in terms of the free base.

27. The dosage form according to claim 24, wherein said unit dosage form is a capsule or tablet.

28. The dosage form according to claim 27, wherein said unit dosage form is a capsule filled with said pellets.

29. The dosage form according to claim 28, wherein said pellets have a particle size within the range of 0.85 to 1.7 mm.

30. The dosage from according to claim 29, wherein said pellets have a particle size of 1.4 to 1.7 mm.

31. The dosage form according to claim 26, wherein said dosage form contains 4 mg of zolpidem as said hypnotic agent and said dosage form exhibits a dissolution profile under US Pharmacopoeia XXIII, Dissolution method I, in a basket apparatus at temperature 37° C., in 0.01N HCl medium and at 100 r.p.m., such that at 15 minutes from the start of the dissolution test 3 mg or less of zolpidem is released.

32. The dosage form according to claim 26, wherein said dosage form contains 18 mg of zolpidem as said hypnotic agent and said dosage form exhibits a dissolution profile under US Pharmacopoeia XXIII, Dissolution method I, in a basket apparatus at temperature 37° C., in 0.01N HCl medium and at 100 r.p.m., such that at 15 minutes from the start of the dissolution test 6 mg or less of zolpidem is released.

33. The dosage form according to claim 32, wherein said 8 mg of zolpidem is in the form of zolpidem hydrogentartrate, expressed in terms of the free base.

34. The dosage form according to claim 32, wherein said release profile is such that at 15 minutes from the start of the dissolution test 5 mg or less of zolpidem is released and essentially 8 mg of zolpidem is released 5 hours or less from the start of the dissolution test.

35. The dosage form according to claim 34, wherein said pellets are spherical and monolithic.

36. A method of inducing or maintaining sleep, which comprises administering an effective hypnotic amount of the pellets according to claim 1 to a mammal.

37. The method according to claim 36, wherein said hypnotic agent is zolpidem free base or zolpidem hydrogen tartrate.

38. A pharmaceutically acceptable monolithic spherical pellet comprising microcrystalline cellulose and zolpidem or a pharmaceutically acceptable salt thereof, wherein said pellet does not contain a release rate controlling excipient or coating, does not contain a surface coating, and exhibits a dissolution profile under US Pharmacopoeia XXIII, Dissolution method I, in a basket apparatus at temperature 37° C., in 0.01N HCl medium and at 100 r.p.m., such that at 15 minutes from the start of the test, less than 70% of the zolpidem has been released from the pellet.

* * * * *